United States Patent [19]

Kawashima et al.

[11] Patent Number: 4,732,139
[45] Date of Patent: Mar. 22, 1988

[54] ENDOSCOPE WITH INSERTION HAVING A PLURALITY OF INSERTION HOLES

[75] Inventors: Masahiro Kawashima; Kunio Ohno; Koji Kambara; Nobuaki Akui; Yoshio Tashiro, all of Tokyo, Japan

[73] Assignee: Olympus Optical Co., Ltd., Japan

[21] Appl. No.: 902,432

[22] Filed: Aug. 29, 1986

[30] Foreign Application Priority Data

| Sep. 3, 1985 | [JP] | Japan | 60-194362 |
| Sep. 19, 1985 | [JP] | Japan | 60-207009 |
| Sep. 19, 1985 | [JP] | Japan | 60-207010 |
| Oct. 28, 1985 | [JP] | Japan | 60-239581 |
| Oct. 30, 1985 | [JP] | Japan | 60-243378 |

[51] Int. Cl.$^4$ ............................................. A61B 1/00
[52] U.S. Cl. ........................................................ 128/6
[58] Field of Search .......................... 128/3, 4, 5, 6, 7; 350/96.26

[56] References Cited

U.S. PATENT DOCUMENTS

| 3,081,767 | 3/1963 | Hett | 128/6 |
| 3,818,902 | 6/1974 | Kinoshita et al. | 128/6 |
| 4,146,019 | 3/1979 | Bass et al. | 128/6 |
| 4,163,148 | 7/1979 | Fritsche et al. | 350/96.26 X |
| 4,615,332 | 10/1986 | Buess et al. | 128/6 |
| 4,617,914 | 10/1986 | Ueda | 128/4 |

FOREIGN PATENT DOCUMENTS 2915425 10/1982 Fed. Rep. of Germany .
WO85/02101 5/1985 PCT Int'l Appl. .

Primary Examiner—William H. Grieb

[57] ABSTRACT

An endoscope includes an operation section and an insertion section extending from the operation section. The insertion section has a plurality of insertion holes extending in its axial direction. The insertion holes have outlet openings open to the distal end portion of the insertion section and inlet openings open to the proximal end portion of the insertion section. One of the inlet openings is open to the proximal end face of the insertion section, and the remaining openings are open to the outer periphery of the insertion section. An image guide and a light guide inserted into the insertion holes extend from the inlet openings located at the outer periphery of the insertion section toward the outside thereof.

16 Claims, 32 Drawing Figures

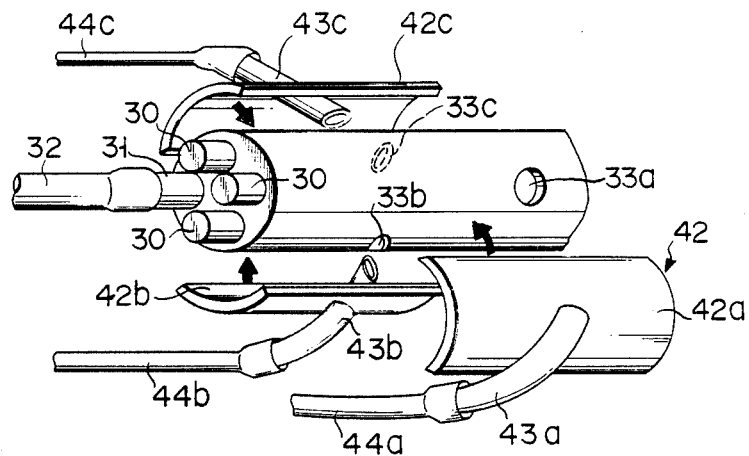
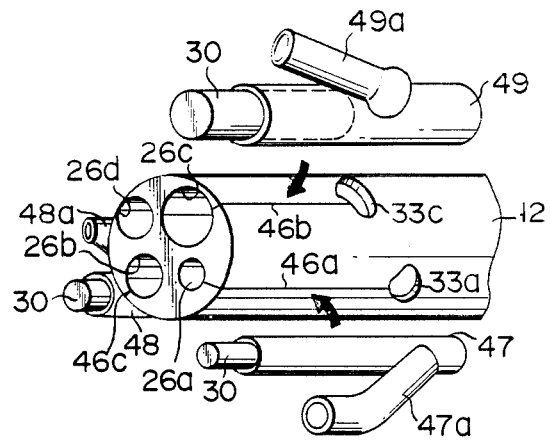
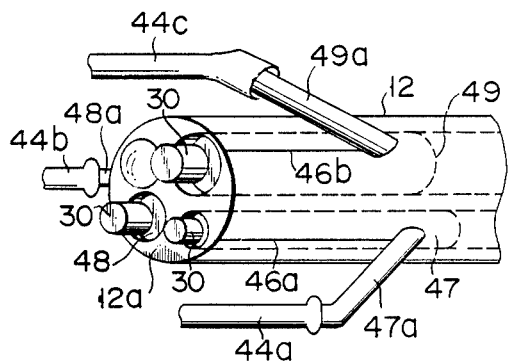

F I G. 14
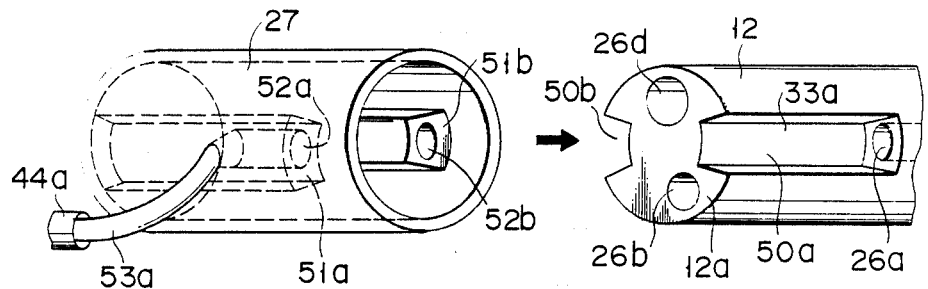
F I G. 15
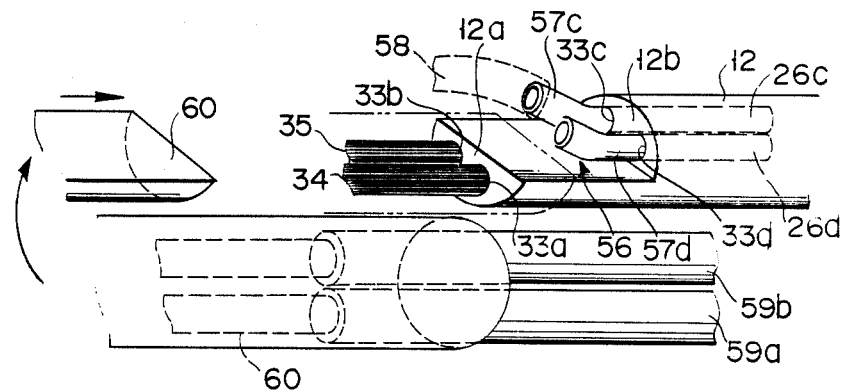
F I G. 16
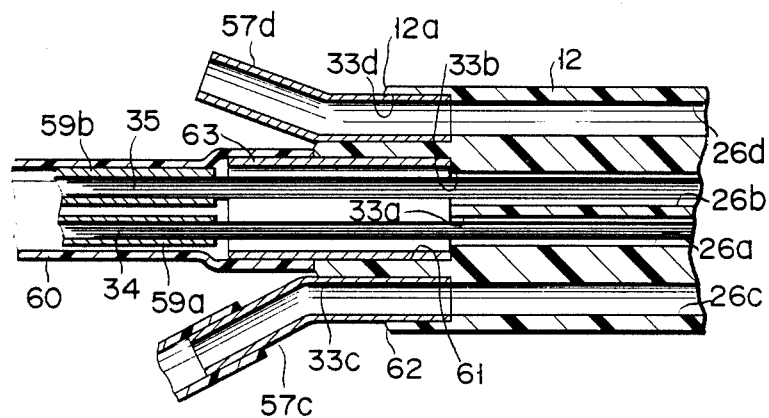

ENDOSCOPE WITH INSERTION HAVING A PLURALITY OF INSERTION HOLES

BACKGROUND OF THE INVENTION

The present invention relates to an endoscope comprising an insertion section having a plurality of insertion holes.

In recent years, an endoscope in which a multihole tube having a plurality of insertion holes has been proposed. These holes serve as guide channels for a light guide, an image guide, and the like, or a tool insertion channel, or an air/liquid-supply channel. In order to decrease the diameter of the insertion section, light and image guides are inserted directly in the insertion holes without being covered with outer tubes. The inlet openings of the respective holes are open to the end face of the insertion section at the operation section side. The light and image guides extend from the inlet openings, and various tubes are connected to the inlet openings of the tool insertion channel and the air/liquid-supply channel. For this reason, various members are concentrated near the end face of the insertion section, and this makes it difficult to satisfactorily keep the respective members separate and limit their arrangement. In addition, design and assembly of the inlet openings and surrounding portions are limited. Furthermore, the light guide and image guide may be interfered with other members to be damaged.

SUMMARY OF THE INVENTION

The present invention has been made in consideration of the above situation and has as its object to provide an endoscope in which respective members connected to inlet openings of an insertion portion can be easily arranged and assembled.

In order to achieve the above object, according to the endoscope of the present invention, an inlet opening of at least one of insertion holes of the insertion section is formed, spaced from the other inlets.

BRIEF DESCRIPTION OF THE DRAWINGS

FIGS. 1 to 4 show an endoscope according to a first embodiment of the present invention, in which FIG. 1 is a side view of the endoscope, FIG. 2 is a perspective view showing the distal end portion of an insertion section, FIG. 3 is a sectional view of the proximal end portion of the insertion section, and FIG. 4 is a perspective view showing the proximal end portion of the insertion section and a receiving member;

FIG. 9 is a perspective view of the proximal end portion of the insertion section of an endoscope according to a second embodiment of the present invention;

FIGS. 10 and 11 are an exploded perspective view and a perspective view of the proximal end portion of the insertion section of an endoscope according to a third embodiment of the present invention;

FIG. 14 is a perspective view of the proximal end portion of the insertion section according to a modification of the present invention;

FIG. 15 is a perspective view of the proximal end portion of the insertion section of an endoscope according to a fifth embodiment of the present invention;

FIG. 16 is a sectional view of the proximal end portion of the insertion section of an endoscope according to a sixth embodiment of the present invention;

FIGS. 25 and 26 show the proximal end portion of the insertion section of an endoscope according to a twelfth embodiment of the present invention, in which FIG. 25 is a sectional view of the proximal end portion before machining and FIG. 26 is a sectional view of the proximal end portion after machining;

DETAILED DESCRIPTION OF THE PREFERRED EMBODIMENTS

An embodiment of the present invention will be described with reference to the accompanying drawings.

Figure 1:
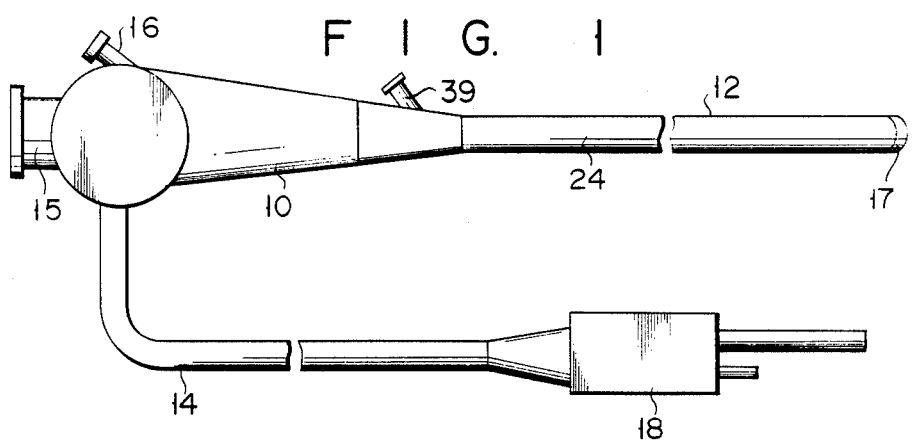
Figure 2:
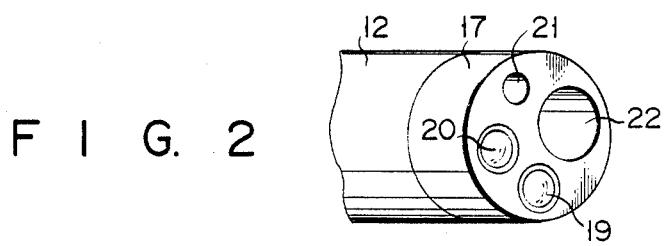

FIG. 1 shows a blood vessel endoscope according to a first embodiment of the present invention. The endoscope comprises operation section 10, insertion section 12 extending from operation section 10 and inserted in a body cavity, and universal cord 14 extending from operation section 10. Eyepiece 15 and tool insertion mouthpiece 16 are mounted on portion 10. Distal end structure 17 is fixed to the extended end of insertion section 10 and connector 18 is fixed to the extended end of universal cord 14. As shown in FIG. 2, objective lens 19 is arranged on distal end structure 17, and light guide opening 20, liquid supply channel opening 21, and tool channel opening 22 are formed in structure 17.

Figure 3:
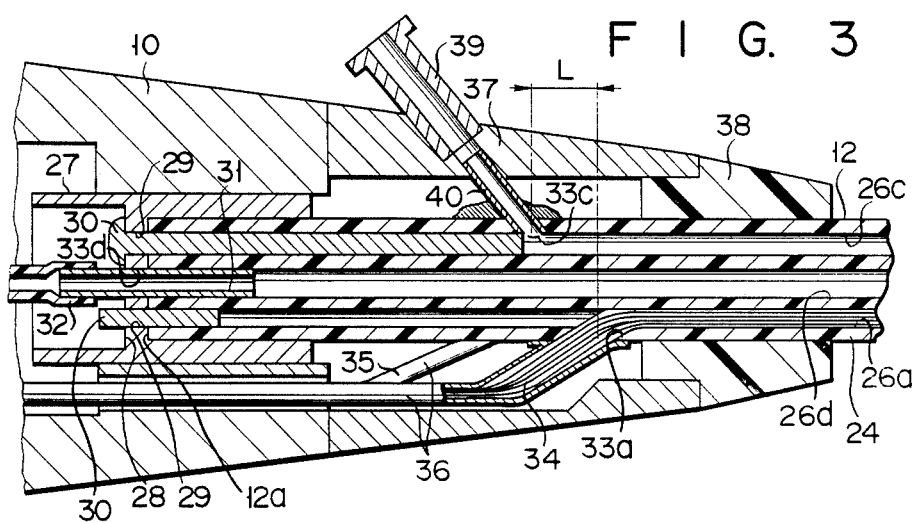
Figure 4:
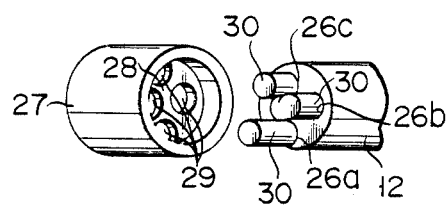

As shown in FIG. 3, insertion section 12 consists of multi-hole tube 24 formed of a flexible resin, e.g., polyurethane or polyethylene. Tube 24 has four insertion holes 26a to 26d extending therethrough along its axis, and these insertion holes 26a to 26d respectively serve as an image guide channel, a light guide channel, a liquid supply channel, and a tool insertion channel. Outlet openings of insertion holes 26a to 26d are connected to objective lens 19, light guide opening 20, liquid supply opening 21, and tool channel opening 22, respectively, arranged in end structure 17. The other end of each of insertion holes 26a to 26d is open to proximal end face 12a of insertion section 12. The proximal end portion of insertion section 12 is inserted in and fixed to cylindrical tube receiving member 27 which is fixed inside the distal end portion of operation section 10. As shown in FIGS. 3 and 4, partition wall 28 is formed on the middle portion of member 27, and insertion section 12 is held in a state wherein its proximal end face 12a abuts against partition wall 28. Four through holes 29 are formed in partition wall 28, and their sizes and positions correspond to those of insertion holes 26a to 26d. Pins 30 are liquid-tightly inserted in and fixed to the proximal end sides of insertion holes 26a, 26b, and 26c through through holes 29. The proximal end opening of channel 26d defines inlet opening 33d, and connecting pipe 31 is inserted in and fixed to opening 33d through through hole 29 to extend backward from receiving member 27. One end of connecting tube 32 is connected to the extended end of pipe 31, and its other end is connected to tool insertion mouthpiece 16 of operating portion 10. Inlet openings 33a, 33b, and 33c respectively communicating with insertion holes 26a, 26b, and 26c are formed in the outer peripheral wall of insertion portion 12 at its proximal end side. Inlet openings 33a, 33b, and 33c extend obliquely backward. Inlet opening 33c is formed to be shifted from inlet openings 33a and 33b toward the operation section 10 side by length L. Cylindrical cover 37 is arranged outside the proximal end portion of insertion section 12 to surround inlet openings 33a, 33b, and 33c, and is fixed to the distal end of operation section 10. Cylindrical bend-preventive tube 38 formed of an elastic member is fitted around the outer periphery of the proximal end portion of insertion section 12 and the distal end of cover 37.

Image guide 34 is inserted in insertion hole 26a, and its distal end is optically connected to objective lens 19. The proximal end portion of image guide 34 extends from inlet opening 33a toward the outside of insertion section 12 to eyepiece 16 of operation section 10. Light guide 35 is inserted in insertion hole 26b, and its distal end is fixed inside light guide opening 20 of end structure 17. The proximal end portion of light guide 35 extends from inlet opening 33b toward the outside of insertion section 12 to connector 18 through operating section 10 and universal cord 14. Protective tubes 36 cover the outer peripheries of portions of image and light guides 34 and 35 extending from insertion section 12. One end portion of outlet pipe 40 is fitted into inlet opening 33c of insertion hole 26c, and the other end thereof communicates with liquid supply mouthpiece 39 fixed to cover 37.

According to the endoscope with the above arrangement, inlet opening 33d of insertion hole 26d is formed in the proximal end face 12a of insertion section 12, and inlet openings 33a to 33c of insertion holes 26a to 26c are formed in the peripheral wall thereof. Inlet openings 33a and 33b and inlet opening 33c are formed to be separated by length L along the axial direction of insertion section 12. For this reason, image guide 34 and light guide 35 extending from inlet openings 33a and 33b, and pipes 40 and 31 connected to inlet openings 33c and 33d will not be concentrated and interfere with each other. Therefore, respective members inserted in or connected to the insertion holes can be arranged with an enough margin, and the endoscope can be easily assembled. In addition, the image and light guides can be prevented from damage.

Figure 5:
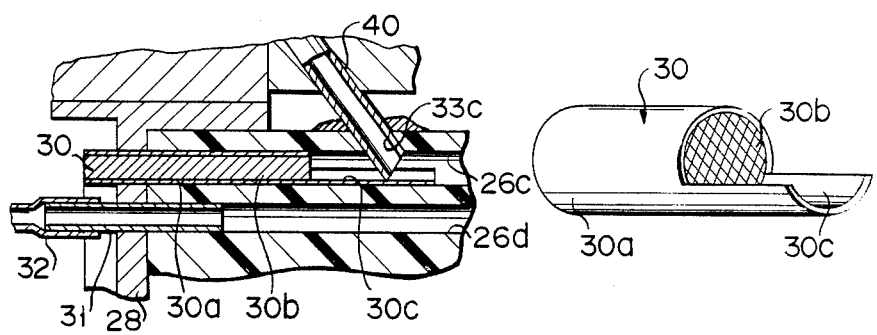
FIGS. 5 and 6 are a sectional view and a perspective view showing a modification of an outlet pipe.
Figure 6:
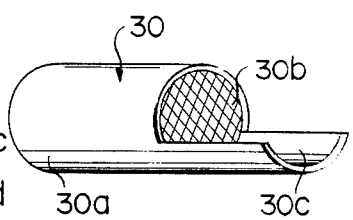

In the first embodiment, pin 30 inserted in insertion hole 26c can be formed by pipe 30a and filler 30b filled therein, as shown in FIGS. 5 and 6. The distal end portion of pipe 30a is cut off excluding a given portion, thus forming tongue portion 30c. Tongue portion 30c is located to face inlet opening 33c, and one end of outlet pipe 40 is inserted in insertion hole 26c through inlet opening 33c and abuts against tongue portion 30c. Therefore, when pipe 40 is inserted in inlet opening 33c the distal end of pipe 40 will not damage the inner surface of tube 24 or will not penetrate through it. The insertion length of pipe 40 can be accurately regulated, thus allowing easy assembly.

Figure 7:
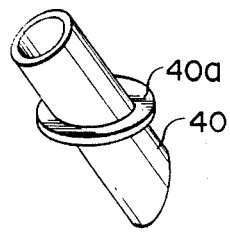
FIGS. 7 and 8 are a perspective view and a sectional view showing another modification of the outlet pipe.
Figure 8:
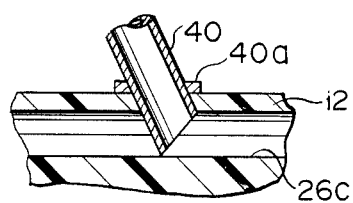

As shown in FIGS. 7 and 8, flange 40a may be formed midway along the outer periphery of outlet pipe 40. When pipe 40 is inserted in inlet opening 33c, flange 40a abuts against the outer peripheral surface of insertion section 12, and the insertion length can be accurately regulated.

FIG. 9 shows a second embodiment of the present invention.

With this embodiment, cylindrical cover 42 is fixed to the outer periphery of the proximal end portion of insertion section 12. Cover 42 is divided into three sections 42a, 42b, and 42c, and these sections are arranged to face inlet openings 33a, 33b, and 33c, respectively. Outlet pipes 43a, 43b, and 43c extend through and are fixed to sections 42a, 42b, and 42c, and are inserted in inlet openings 33a, 33b, and 33c, respectively. The extended ends of pipes 43a, 43b, and 43c are connected to image guide outer tube 44a, light guide outer tube 44b, and liquid supply tube 44c, respectively.

With the second embodiment, when sections 42a, 42b, and 42c are fixed to the outer peripheral surface of insertion section 12, outlet pipes 43a, 43b, and 43c can be connected to inlet openings 33a, 33b, and 33c, thus allowing easy assembly.

With an embodiment shown in FIGS. 10 and 11, slits 46a, 46b, and 46c are formed in the proximal end portion of insertion section 12 and extend from inlet openings 33a, 33b and 33c to end face 12a of section 12 along the axial direction thereof. Pipe 47 is inserted in the proximal end portion of insertion hole 26a. Pipe 47 has branch pipe 47a, which extends from inlet opening 33a toward the outside of insertion section 12. Similarly, pipes 48 and 49 are inserted in the proximal end portions of insertion holes 26b and 26c, respectively, and have branch portions 48a and 48b extending from inlet openings 33b and 33c, respectively. Pins 30 are liquid-tightly inserted in pipes 47, 48, and 49. The extended ends of branch portions 47a, 47b, and 47c are connected to image guide outer tube 44a, light guide outer tube 44b, and liquid supply tube 44c, respectively.

Pipes 47, 48, and 49 are inserted in corresponding insertion holes by utilizing slits 46a, 46b, and 46c, respectively and are fixed therein by fixing slits with an adhesive. Since pipes 47, 48, and 49 are inserted in insertion holes 26a, 26b, and 26c through slits 46a, 46b, and 46c the endoscope can be easily assembled.

Figure 12:
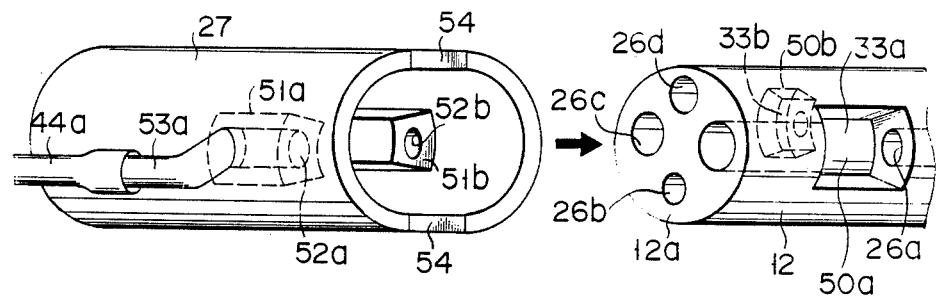
FIGS. 12 and 13 are an exploded perspective view and a perspective view of the proximal end portion of the insertion section of an endoscope according to a fourth embodiment of the present invention.
Figure 13:
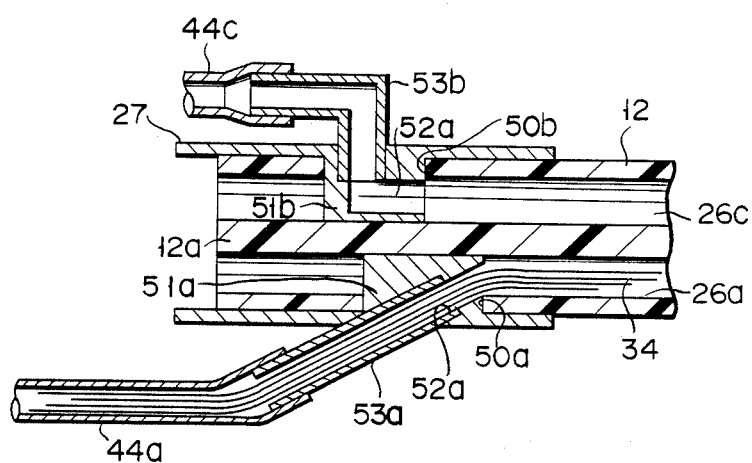

According to a fourth embodiment shown in FIGS. 12 and 13, inlet openings 33a and 33c of insertion holes 26a and 26c are defined by rectangular recesses 50a and 50b formed in the outer peripheral wall of insertion section 12. Projections 51a and 51b to be fitted in recesses 50a and 50b are formed in the inner peripheral surface of tube receiving member 27 which is fitted on the proximal end portion of insertion section 12. Paths 52a and 52b respectively communicating with insertion holes 26a and 26c are formed in projections 51a and 51b, respectively. Outlet pipes 53a and 53b respectively communicating with paths 52a and 52b extend from member 27. The projecting ends of pipes 53a and 53b are respectively connected to image guide outer tube 44a and liquid supply tube 44c.

A pair of axial slits 54 are formed in tube receiving member 27. When member 27 is fitted around insertion section 12, it is extended by utilizing slits 54, and is mounted on the proximal end portion of insertion section 12 so that projections 51a and 51b are fitted in recesses 50a and 50b, respectively. Thereafter, member 27 is liquid-tightly fixed to the outer peripheral surface of insertion section 12 by an adhesive.

With the fourth embodiment, outlet pipes 53a and 53b can be easily connected to insertion holes 26a and 26c to allow easy assembly, and insertion section 12 can be accurately aligned with operating section 10.

As shown in FIG. 14, in the fourth embodiment, recesses 50a and 50b can extend to end face 12a of insertion section 12. In this case, projections 51a and 51b also extend to the proximal end of tube receiving member 27. With this arrangement, member 27 can be fitted to insertion section 12 without forming slits 54 in member 27.

FIG. 15 shows a fifth embodiment of the present invention. According to this embodiment, the upper half of the proximal end portion of insertion section 12 is cut off to form stepped portion 56. Therefore, insertion section 12 has semicircular first end face 12a located at its proximal end and semicircular second end face 12b located at a position shifted from first end face 12a toward the distal end of section 12. Inlet openings 33a and 33b of image guide insertion hole 26a and light guide insertion hole 26b extending through insertion section 12 are open to first end face 12a. Outlet openings 33c and 33d of liquid supply insertion hole 26c and tool insertion hole 26d are open to second end face 12b. Connecting pipes 57c and 57d are respectively connected to inlet openings 33c and 33d. The projecting portions of pipes 57c and 57d are bent in a direction to separate from insertion section 12. The extended end of connecting pipe 57c is connected with liquid supply tube 58, which extends to connector 18 through operation section 10 and universal cord 14 (FIG. 1). The extended end of pipe 57d is connected with a guide tube (not shown), which is connected to tool insertion mouthpiece 16 (FIG. 1) through operation section 10.

Image guide 34 extends from insertion hole 26a toward the outside of insertion section 12 through inlet opening 33a, and light guide 35 extends from insertion hole 26b toward the outside of section 12 through inlet opening 33b. The extended portions of image guide 34 and light guide 35 are covered with outer tubes 59a and 59b, respectively. In addition, image guide 34 and light guide 35 are inserted in protective tube 60, the distal end of which is fitted around the proximal end of insertion section 12 to cover inlet openings 33a and 33b.

According to the fifth embodiment as described above, inlet openings 33a to 33d of insertion holes 26a to 26d are separately open to first and second end faces 12a and 12b which are spaced along the axial direction of insertion section 12. For this reason, the respective components extending from the inlet openings will not be concentrated, and can be arranged with an enough margin. Therefore, the endoscope can be easily assembled, and the image guide and the light guide will not interfere with other components to be damaged.

According to a sixth embodiment shown in FIG. 16, circular recess 61 is formed at the center of proximal end face 12a of insertion section 12. Proximal end face 12a is tapered to form tapered surface 62. Inlet opening 12a of insertion hole 26a for image guide 34 and inlet opening 33b of insertion hole 26b for light guide 35 are open to the bottom of recess 61. Image guide 34 and light guide 35 extend from inlet openings 33a and 33b toward the outside of insertion section 12. Recess 61 is fitted with one end of connecting pipe 63, and the other end portion of pipe 63 extends backward from insertion section 12. The other end of pipe 63 is connected to protective tube 60, and image guide 34 and light guide 35 are inserted in tube 60 through connecting pipe 63. In addition, the outer peripheral surfaces of image guide 34 and light guide 35 are covered with outer tubes 59a and 59b, respectively.

Inlet opening 33c of liquid supply insertion hole 26c and inlet opening 33d of tool insertion hole 26d are open to tapered surface 62. Inlet openings 33c and 33d are respectively connected to connecting pipes 57c and 57d, which project from tapered surface 62. The projecting portions of pipes 57c and 57d are bent outward to be separated from connecting pipe 63.

In the sixth embodiment, since inlet openings 33a to 33d are arranged separately, the same effect as in the fifth embodiment can be obtained.

Figure 17:
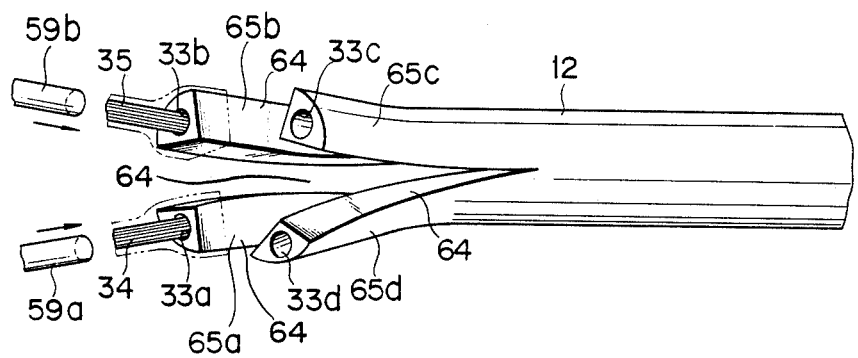
FIG. 17 is a perspective view of the proximal end portion of the insertion section of an endoscope according to a seventh embodiment of the present invention.

According to a seventh embodiment shown in FIG. 17, four notches 64 are formed in the proximal end portion of insertion section 12 along its axial direction. The proximal end portion is divided into four sections 65a to 65d by notches 64, and these sections are branched radially. Inlet openings 33a to 33d of insertion holes 26a to 26d are formed in the distal end faces of sections 65a to 65d, respectively. Image and light guides 34 and 35 extending from inlet openings 33a and 33b are covered with outer tubes 59a and 59b, respectively. The distal ends of tubes 59a and 59b are fitted or the end portions of sections 65a and 65b, respectively, as indicated by two-dots and dash lines in FIG. 17.

Figure 18:
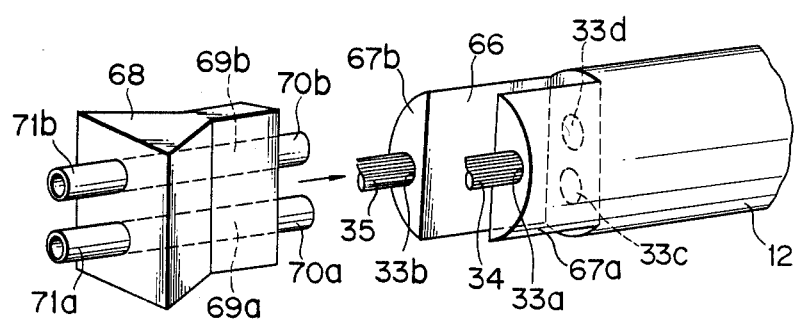
FIGS. 18 and 19 are an exploded perspective view and a sectional view of the proximal end portion of the insertion section of an endoscope according to an eighth embodiment of the present invention.
Figure 19:
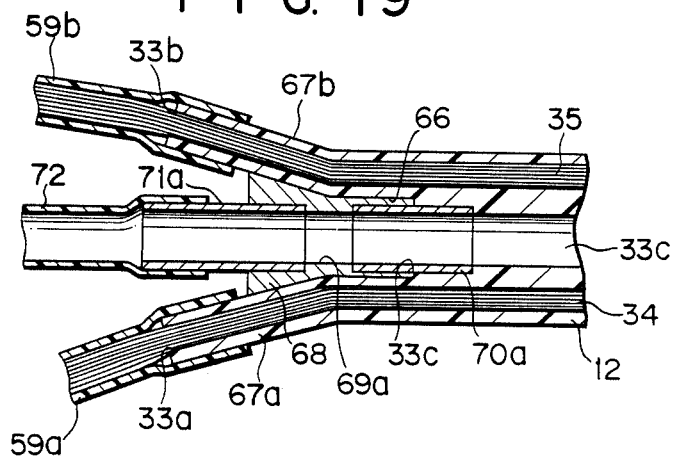

According to an eighth embodiment shown in FIGS. 18 and 19, recess 66 is formed in the proximal end portion of insertion section 12 to define a pair of opposite projections 67a and 67b separated at a given distance. Inlet opening 33a of insertion hole 26a for image guide 34 is open to the distal end face of projection 67a, and inlet opening 33b of insertion hole 26b for light guide 35 is open to the distal end face of projection 67b. Inlet opening 33c of liquid supply insertion hole 26c and inlet opening 33d of tool insertion hole 26d are open to the bottom of recess 66. Image guide 34 extending from inlet opening 33a is covered with outer tube 59a, and the distal end of tube 59a is fitted on projection 67a. Similarly, light guide 35 extending from inlet opening 33b is covered with outer tube 59b, and the distal end of tube 59b is fitted on projection 67b.

Wedge-shaped pressing member 68 is pressed in recess 66, thereby biasing projections 67a and 67b in opposite directions. A pair of parallel through holes 69a and 69b are formed in pressing member 68. One end of each of through holes 69a and 69b receives one end of each of coupling pipes 70a and 70b, and the other end thereof receives one end of each of connecting pipes 71a and 71b. The other end of each of coupling pipes 70a and 70b is respectively inserted in inlet opening 33c or 33d. The other end of coupling pipe 71a is connected to liquid supply tube 72, and that of connecting pipe 71b is connected to a guide tube (not shown).

According to the seventh and eighth embodiments as described above, inlet openings 33a to 33d of insertion holes 26a to 26d can be formed to be sufficiently separated from one another, and the same effect as in the fifth embodiment can be obtained.

Figure 20:
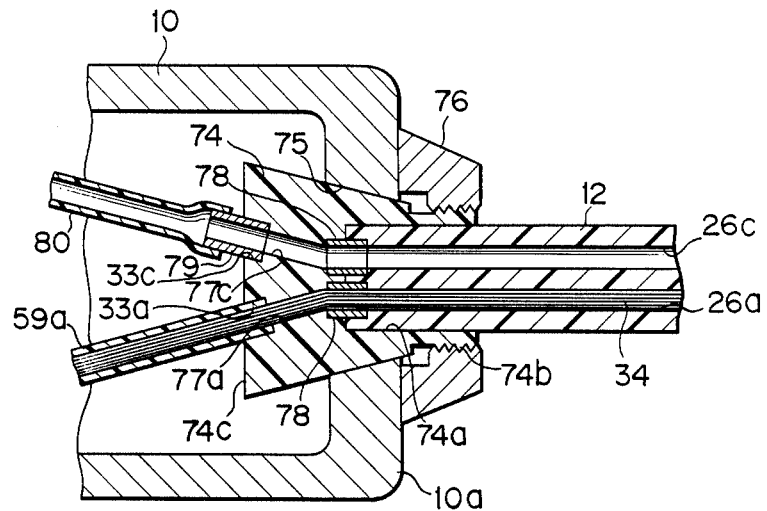
FIG. 20 is a sectional view of the proximal end portion of the insertion section of an endoscope according to a ninth embodiment of the present invention.

FIG. 20 shows a ninth embodiment of the present invention. With this embodiment, the proximal end portion of insertion section 12 is connected to truncated conical connecting member 74. More specifically, circular recess 74a is formed in the end face of connecting member 74 at its small diameter side, and the proximal end portion of insertion section 12 is liquidtightly fitted in recess 74a. Connecting member 74 is inserted in engaging hole 75 formed in the distal end of operation section 10. Engaging hole 75 has a tapered inner peripheral surface corresponding to connecting member 74. Threaded portion 74b is formed on the outer periphery of the small-diameter end portion of member 74. Fixing ring 76 is screwed with threaded portion 74b from the outside of operation section 10 to abut against distal end face 10a of section 10. Thus, connecting member 74 is fixed to section 10 while its peripheral surface is in tight contact with the inner peripheral surface of engaging hole 75.

Four through holes 77a to 77d (only holes 77a and 77c are shown) communicating with insertion holes 26a to 26d of insertion section 12 are formed in connecting member 74. Each through hole has one end open to the bottom of recess 74a and the other end open to large-diameter side end face 74c of member 74. Through holes 77a to 77d extend radially so that distances therebetween at the end face 74c side are larger than those at the recess 74a side. The other-end openings of through holes 77a to 77d respectively define inlet openings 33a to 33d of insertion holes 26a to 26d. These through holes are connected to the corresponding insertion holes through pipes 78 inserted therein. The outer peripheral surface of image guide 34 extending in operation section 10 through insertion hole 26a and through hole 77a is covered with outer tube 59a. The distal end portion of tube 59a is fitted in inlet opening 33a. One end of connecting pipe 79 is fitted in inlet opening 33c, and the other end thereof is connected to liquid supply tube 80.

According to the endoscope with the above arrangement, through holes 77a to 77d formed in connecting member 74 extend radially from insertion section 12 toward operation section 10, and distances between inlet openings 33a to 33d are sufficiently large. For this reason, connection of pipes to the inlet openings and insertion of the image guide can be easily performed. The image and light guides will not interfere with each other or with other members to be prevented from being damaged. Since the outer peripheral surface of connecting member 74 is held in tight contact with the tapered inner peripheral surface of engaging hole 75, operation and insertion sections 10 and 12 can be easily and reliably aligned with each other.

Figure 21:
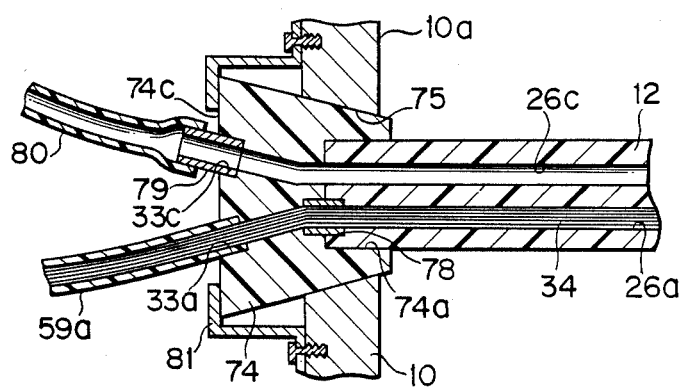
FIG. 21 is a sectional view showing a modification of a fixing means.

Note that connecting member 74 may be fixed to operation section 10 by fixing plate 81, as shown in FIG. 21. More specifically, fixing plate 81 is fixed to the inner surface of section 10 by screws, and connecting member 74 is urged against the inner peripheral surface of engaging hole 75 by fixing plate 81 from the side of section 10.

Figure 22:
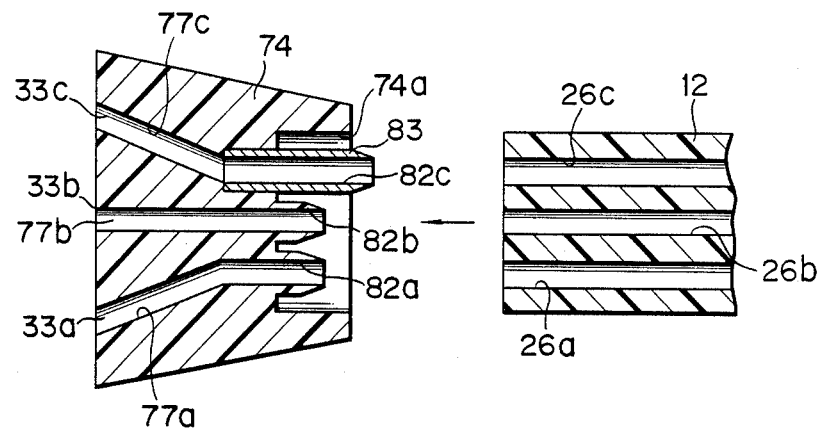
FIG. 22 is a sectional view of the proximal end portion of the insertion section of an endoscope according to a tenth embodiment of the present invention.

According to a tenth embodiment shown in FIG. 22, connecting member 74 has a plurality of pipe-like projections 82a to 82d (82d is not shown) projecting from the bottom of recess 74a toward insertion section 12. Projections 82a to 82d communicate with through holes 77a to 77d, respectively. Projections 82a and 82b are formed integrally with connecting member 74, and projection 82c is constituted by pipe 83 inserted in through hole 77c. Pipe 83 is longer than other projections.

When insertion section 12 is connected to connecting member 74, the distal end portion of projection 82c is inserted in insertion hole 26c. In this state, after insertion holes 26a and 26b are aligned with projections 82a and 82b, insertion section 12 is fitted into recess 74a.

With this arrangement, when connecting member 74 is connected to insertion section 12, projection 82c can be used as a guide member, thus allowing easy assembly. Note that projection 82c can be integrally formed with connecting member 74.

Figure 23:
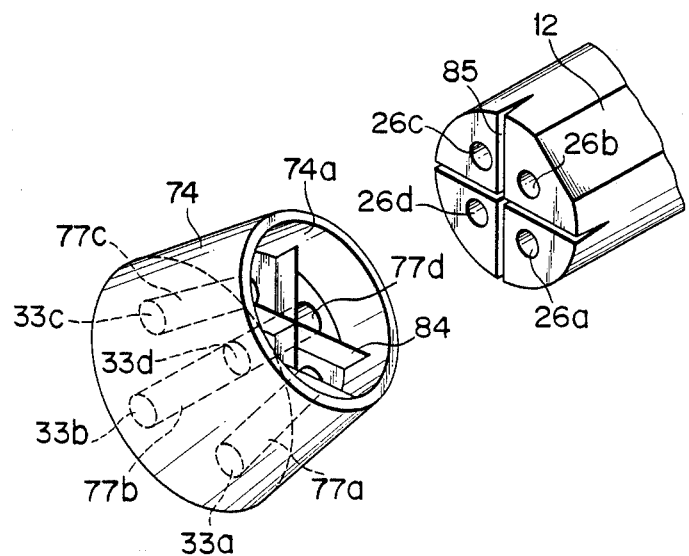
FIG. 23 is a perspective view of the proximal end portion of the insertion section of an endoscope according to an eleventh embodiment of the present invention.

FIG. 23 shows an eleventh embodiment of the present invention. With this embodiment, cross-like partition wall 84 is formed on the bottom of recess 74a of connecting member 74 to partition the openings of through holes 77a to 77d. Cross-like notche 85, in which partition walls 84 is inserted, is formed in proximal end face 12a of insertion section 12.

According to this embodiment, through holes 77a to 77d and insertion holes 26a to 26d can be reliably shielded from one another by utilizing a combination of partition wall 84 and notche 85 without using a special member such as a connecting pipe. The above arrangement improves the mechanical strength of insertion section 12 against torsion. In addition, since a connecting pipe and the like need not be used, assembly is easy.

In the eleventh embodiment, partition wall 84 may be formed on proximal end face 12a of insertion section 12 and notche 85 may be formed in the bottom of recess 74a.

Figure 24:
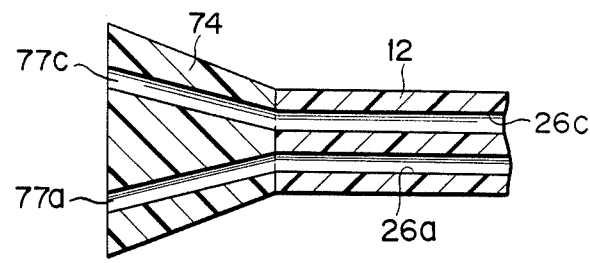
FIG. 24 is a sectional view showing a modification of the proximal end portion of the insertion portion.

As shown in FIG. 24, connecting member 74 may be fixed directly to the proximal end face of insertion section 12 by welding or an adhesive.

Figure 25:
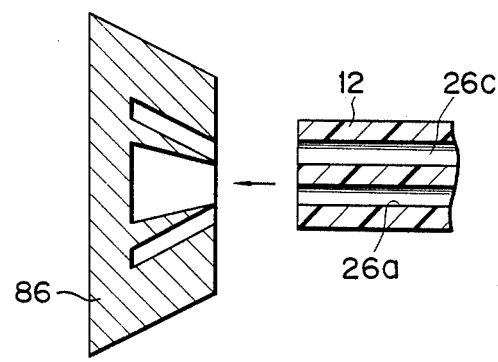
Figure 26:
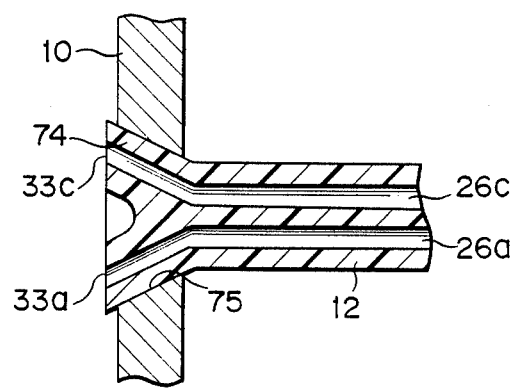

According to a twelfth embodiment shown in FIGS. 25 and 26, connecting member 74 is formed integrally with insertion section 12. The proximal end portion of section 12 is hot-pressed in metal mold 86 so as to be formed in the same shape as that of tapered connecting member 74. In this case, a connecting operation of member 74 and section 12 can be omitted, thus making the assemling operation easier.

Figure 27:
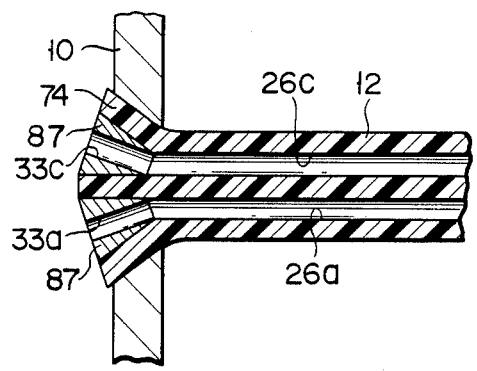
FIG. 27 is a sectional view of the proximal end portion of the insertion section of an endoscope according to a thirteenth embodiment of the present invention.

According to a thirteenth embodiment shown in FIG. 27, conical hollow pins 87 are pressed into inlet openings 33a to 33d of insertion holes 26a to 26d, respectively. Thereby, the proximal end portion of insertion section 12 forms tapered connecting portion 74.

Figure 28:
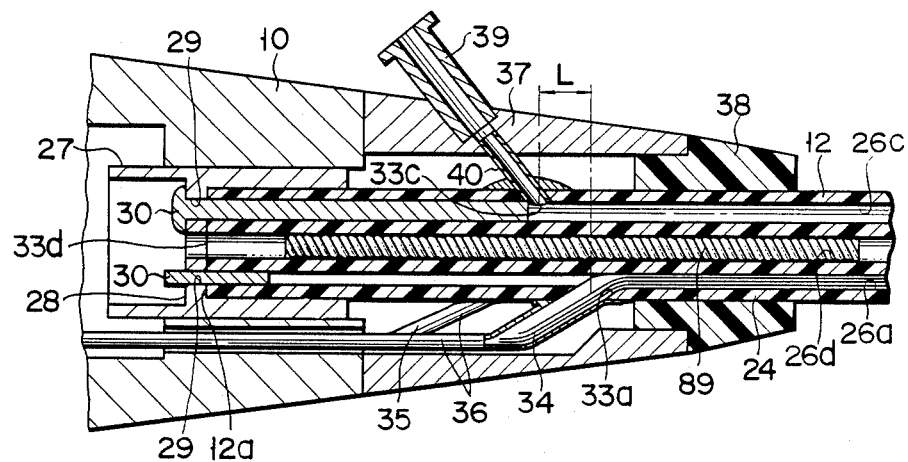
FIG. 28 is a sectional view of the proximal end portion of the insertion section of an endoscope according to a fourteenth embodiment of the present invention.

According to a fourteenth embodiment shown in FIG. 28, elongated elastic member 89 is inserted in insertion hole 26d and is fixed at a predetermined position. Elastic member 89 extends from the proximal end portion of section 12 to the distal end side thereof over bend-preventive member 38. Member 89 is formed by twisting wires.

With this embodiment, when insertion section 12 is bent, bend-preventive member 38 and elastic member 89 are elastically deformed to absorb a bending stress acting on section 12. Since elastic member 89 extends over member 38, the flexibility of section 12 moderately changes at a boundary between portions with and without bend-preventive member 38. Therefore, insertion section 12 can be prevented from being broken upon abruptly change in flexibility at the boundary. The flexibility of section 12 at the boundary can be desirably set by changing the diameter of wires constituting elastic member 89.

Note that elastic member 89 need not be formed by twisting wires, but can be formed by a rod or coil formed of a given elastic material. Alternatively, a synthetic resin adhesive may be filled in the insertion hole and solidified to form an elastic member.

Figure 29:
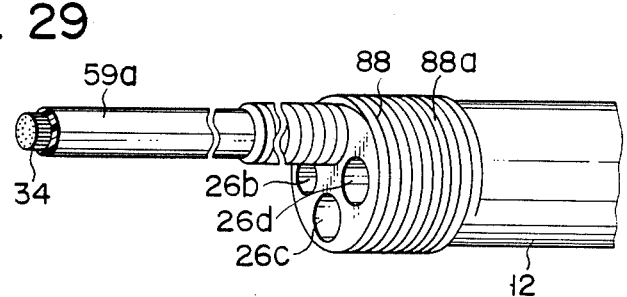
FIGS. 29 and 30 are a perspective view and a sectional view of the proximal end portion of the insertion section of an endoscope according to a fifteenth embodiment of the present invention.
Figure 30:
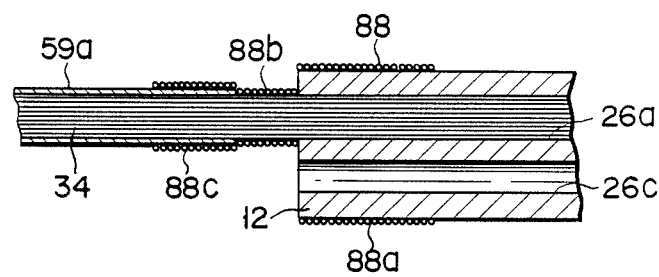

FIGS. 29 and 30 show a fifteenth embodiment of the present invention. With this embodiment, outer tube 59a covering the outer peripheral surface of image guide 34 extends to a portion separated from proximal end face 12a of insertion section 12 at a given distance. As a result, image guide 34 is exposed at a portion near proximal end face 12a. Single elastic coil 88 is wound around the outer periphery of insertion section 12, the exposed portion of image guide 34, and the outer periphery of the distal end portion of outer tube 59a. Portion 88a of coil 88 located at the outer periphery of section 12 is tightly and strongly wound. Portion 88b located at the exposed portion of image guide 34 is softly wound but not to be loosened. Portion 88c located at the outer periphery of outer tube 59a is tightly and strongly wound.

With this embodiment, since single coil 88 is wound around the proximal end portion of insertion section 12, the exposed portion of image guide 34, and the distal end portion of outer tube 59a, the flexibility of the exposed portion of image guide 34 will not abruptly change with respect to that of section 12 and outer tube 59a. Therefore, when insertion section 12 is bent, image guide 34 can be prevented from being broken at its exposed portion.

Figure 31:
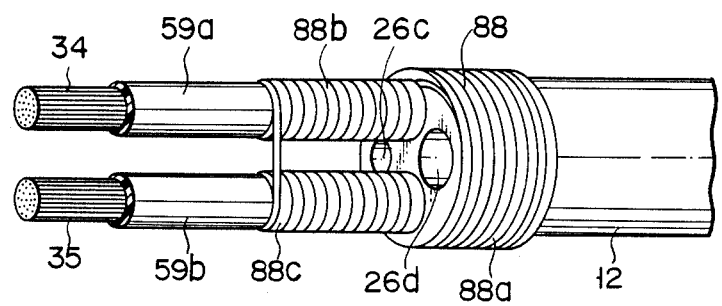
FIGS. 31 and 32 are perspective views showing the proximal end portion of the insertion section of an endoscope according to sixteenth and seventeenth embodiments of the present invention.
Figure 32:
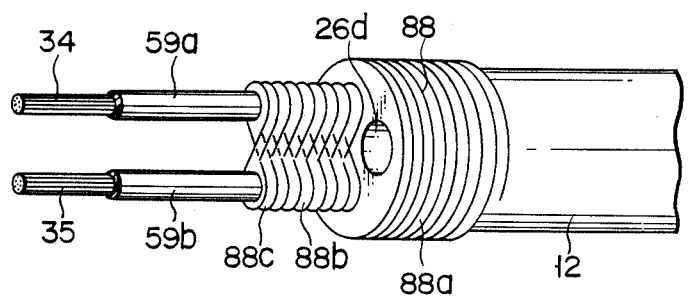

As shown in FIGS. 31 and 32, coil 88 may also be wound around the exposed distal end portion of light guide 35 in addition to image guide 34. In this case, image and light guides 34 and 35 can be prevented from being bent, and the distance therebetween can be held constant, thereby preventing interference and damage thereof.

What is claimed is:

1. An endoscope comprising:
an operation section;
a flexible insertion section extending from said operation section and adapted to be inserted in a body cavity, said insertion section having a plurality of insertion holes extending along its axial direction, each of said insertion holes having an outlet opening open to a distal end portion of said insertion section and an inlet opening open to a proximal end portion of said insertion section, and at least one of said inlet openings being formed to be separated from other inlet openings; and a plurality of components inserted in said insertion holes and extending from said inlet openings toward the outside of said insertion section, said components including an optical fiber which is inserted in the insertion hole having said one inlet opening.

2. An endoscope according to claim 1, wherein said insertion section has a proximal end face perpendicular to its axial direction, at least one of said inlet openings is open to a peripheral surface of said insertion section, and the remaining inlet openings are open to said proximal end face.

3. An endoscope according to claim 2, which further comprises: an outlet pipe inserted in the inlet opening open to the peripheral surface of said insertion section from the outside thereof and communicating with corresponding insertion hole.

4. An endoscope according to claim 3, wherein said outlet pipe has a stopper, abutting against the outer peripheral surface of said insertion section, for regulating an insertion length of said outlet pipe.

5. An endoscope according to claim 3, which further comprises: a protective member inserted in said insertion hole having the inlet opening open to the outer peripheral surface of said insertion section and having an extending portion located to face the inlet opening open to the outer peripheral surface, and said outlet pipe having one end abutting against the extending portion.

6. An endoscope according to claim 2, wherein a plurality of said inlet openings are open to the peripheral surface of said insertion section, and are arranged to be shifted from each other along the axial direction of said insertion section.

7. An endoscope according to claim 6, wherein two of said inlet openings are arranged far from the remaining inlet openings toward the distal end side of said insertion section, and said components extending from these two inlet openings consist of optical fibers forming an image guide and a light guide.

8. An endoscope according to claim 1, wherein said insertion section has a first end face perpendicular to its axis and a second end face located to be shifted from said first end face toward the distal end side of said insertion section and perpendicular to the axis of said insertion section, at least one of said inlet openings is open to said second end face, and the remaining inlet openings are open to said first end face.

9. An endoscope according to claim 8, wherein a pair of inlet openings are open to said first end face, and said components extending from said pair of inlet openings consist of optical fibers forming an image guide and a light guide.

10. An endoscope according to claim 1, wherein said insertion section has a proximal end face perpendicular to its axis and a recess formed in said proximal end face, at least one of said inlet openings is open to the bottom of said recess, and the remaining inlet openings are open to said proximal end face.

11. An endoscope according to claim 1, wherein said insertion section has a proximal end face perpendicular to its axis and a recess formed in said proximal end face to define a pair of opposite projections, at least one of said inlet openings is open to the bottom of said recess, and the remaining inlet openings are open to said proximal end face; and which further comprises a wedge-shaped pressing member pressed in said recess to deform said projections in opposite directions, said pressing member having a through hole communicating with the inlet opening open to the bottom of said recess.

12. An endoscope according to claim 1, wherein the proximal end portion of said insertion section has a plurality of radial branch sections, and said inlet openings are respectively open to distal end faces of said branch sections.

13. An endoscope according to claim 1, which further comprises: a connecting member having a truncated conical shape and arranged on the proximal end member of said insertion section, said connecting member having a small-diameter end face located at the side of said proximal end portion of said insertion section, a large-diameter end face located at the side of said operation section, and a plurality of through holes formed to radially extend from the small-diameter end face toward the large-diameter end face, each of said through holes having one end communicating with corresponding insertion hole and the other end open to said large-diameter end face and defining said inlet opening.

14. An endoscope according to claim 13, wherein said connecting member is formed integrally with said insertion section.

15. An endoscope according to claim 1, which further comprises: a cylindrical bend-preventive member which is fitted around the outer periphery of the proximal end portion of said insertion section, fixed to said operation section, and formed of an elastic material, and a reinforcing member inserted in at least one of said insertion holes from its inlet opening and extending toward the distal end side of said insertion section over said bend-preventive member.

16. An endoscope according to claim 1, which further comprises: a single elastic coil wound around the proximal end section of said insertion section and around an insertion-section side end portion of at least one of said components extending from said inlet openings.

* * * * *

UNITED STATES PATENT AND TRADEMARK OFFICE
CERTIFICATE OF CORRECTION

PATENT NO.   : 4,732,139
DATED        : March 22, 1988
INVENTOR(S)  : Masahiro Kawashima, et al It is certified that error appears in the above-identified patent and that said Letters Patent are hereby corrected as shown below:

Title page:

[75]   Inventors:  Masahiro Kawashima; Kunio Ohno;
                   Koji Kambara; Nobuaki Akui; Yoshio Tashiro;
                   Tsuruo Hatori, all of Tokyo, Japan Signed and Sealed this Twentieth Day of September, 1988

Attest:

DONALD J. QUIGG

*Attesting Officer*    *Commissioner of Patents and Trademarks*